United States Patent

Mills et al.

[11] 4,052,467
[45] Oct. 4, 1977

[54] CATALYTIC REDUCTION OF ALDEHYDES TO ALCOHOLS

[75] Inventors: King L. Mills; Roy V. Denton, both of Bartlesville, Okla.

[73] Assignee: Phillips Petroleum Company, Bartlesville, Okla.

[21] Appl. No.: 73,584

[22] Filed: Sept. 18, 1970

Related U.S. Application Data

[63] Continuation-in-part of Ser. No. 681,590, Nov. 8, 1967, abandoned.

[51] Int. Cl.$^2$ .................... C07C 29/14; C07C 29/24; C07C 29/16
[52] U.S. Cl. .................... 260/638 B; 260/638 HF; 260/643 B
[58] Field of Search .......... 260/638 HF, 638 B, 643 B

[56] References Cited

U.S. PATENT DOCUMENTS

| 2,549,416 | 4/1951 | Brooks | 260/638 HF |
|---|---|---|---|
| 2,694,091 | 11/1954 | Harvey et al. | 260/638 HF |
| 2,709,714 | 5/1955 | Mertzweiller | 260/638 HF |
| 2,713,075 | 7/1955 | Doeringer et al. | 260/638 HF |

*Primary Examiner*—Joseph E. Evans

[57] ABSTRACT

Aldehydes in a feed containing sulfur in the range of about 10 ppm to 1 weight percent in the form of thiophene or other heterocyclic ring compounds are hydrogenated in admixture with $H_2$ to the corresponding alcohols with a catalyst comprising a reduced mixture of the oxides of Zn and Cu, without decomposing the ring sulfur compounds to a form of sulfur which deactivates the catalyst by using critical reaction conditions.

1 Claim, No Drawings

CATALYTIC REDUCTION OF ALDEHYDES TO ALCOHOLS

This is a continuation-in-part of application Ser. No. 681,590, filed Nov. 8, 1967, now abandoned.

The invention relates to a process for the catalytic reduction of aldehydes to alcohols, using feeds which contain thiophene or other ring-type sulfur compounds in a concentration in the range of about 10 parts per million (ppm) to about 1 weight percent of the feed (calculated as S).

In the oxo process for the formation of aldehydes and alcohols by the reaction of CO and $H_2$ with olefins, it is desirable to catalytically reduce the aldehydes to the corresponding alcohols. There are a number of catalysts which function in this reduction successfully, providing the feed material is relatively sulfur-free, i.e., containing less than 10 ppm of sulfur. However, there are relatively few sulfactive catalysts for this reduction and these are relatively inefficient for the reduction process and also nonselective in the presence of olefins and aromatics.

The instant invention is concerned with a process which efficiently reduces aldehydes to the corresponding alcohols in the presence of thiphene and other ring-type sulfur compounds without decomposing the sulfur compounds to free sulfur and/or sulfur compounds which deleteriously affect the reduction catalyst.

Accordingly, it is an object of the invention to provide a process for the reduction of aldehydes to the corresponding alcohols in feeds containing small amounts of thiophene or other ring-type sulfur compounds without decomposition of these sulfur compounds which deleteriously affects the life of the catalyst. Another object is to provide a catalyst and operating conditions for the reduction of aldehydes to alcohols without deactivation of the catalyst, using a feed containing ring-type sulfur compounds such as thiophene. A further object is to provide a process for reducing aldehydes to the corresponding alcohols in a feed containing ring-type sulfur compounds, olefins, and aromatics which avoids decomposition of the sulfur compounds and deactivation of the catalyst and is selective for the aldehyde reduction. Other objects of the invention will become apparent to one skilled in the art upon consideration of the accompanying disclosure.

A broad aspect of the invention comprises reducing an aldehyde to the corresponding alcohol in a feed containing at least 10 ppm and up to 1 weight percent of sulfur in the form of thiophene or other ring-type sulfur compounds and at least 1 weight percent of an aldehyde of up to and including 30 carbon atoms per molecule, in contact with a catalyst comprising essentially a reduced mixture of the oxides or hydroxides of Zn and Cu at a temperature in the range of 450° to 550° F., a pressure in the range of 800 to 1200 psig, a liquid hourly space rate in the range of 1.0 to 1.5, and an amount of $H_2$ in the reaction mixture sufficient to hydrogenate the aldehyde present in the feed. The process is applicable to aldehydes containing up to and including 30 carbon atoms per molecule but feeds containing $C_4$ to $C_{20}$ are preferred. A feed to which the invention is particularly adapted comprises the hydroformylation reaction effluent resulting from hydroformylation of a heptene fraction containing olefins in the range of about 30 to 80 weight percent, said effluent containing olefins, thiophene, alcohols, and aldehydes. Such a feed is a heptene fraction recovered from a catalytically cracked hydrocarbon feed readily obtainable in conventional refinery operation.

The catalyst before reduction contains from 10 to 60 percent copper oxide (CuO) and from 90 to 40 percent (by weight) of zinc oxide (ZnO). The preferred amount of CuO in the catalyst is in the range of 38 to 41 percent and the balance zinc oxide. An inert carrier material may be included in the catalyst composition. The catalyst may be prepared by fixing the separate oxides, by coprecipitation of the oxylates, carbonates, acetates, etc., followed by calcination. The coprecipitation method is preferred, however, any means known to the art of forming a composite of the copper and zinc oxides can be utilized. The catalyst is reduced in $H_2$ or CO at a temperature in the range of about 400° to 800° F. for at least several hours. While reduction of the catalyst prior to use in the aldehyde reduction is preferred, it may be reduced during the process of conversion of the aldehyde to the alcohol. In the reduction of the catalyst, either $H_2$ or CO reduction may be utilized, alone, in admixture, and mixed with an inert diluent such as steam, nitrogen, combustion gas, etc., Nitrogen is the preferred diluent. The catalyst composite generally is pelleted prior to reduction and use.

The concentration of hydrogen in the reaction zone is not critical, but there should be an excess of hydrogen over stoichiometric in relation to the aldehyde to be reduced. An amount of hydrogen in the range of 4000 to 8000 standard cubic feet per ton of feed (aldehyde) generally is used and preferred.

In order to prevent decomposition of the thiophene or other ring-type sulfur compounds in the feed with attendant deterioration of the catalyst, it is essential to maintain the temperature of the aldehyde reduction reaction in the range of 450° to 550° F., the pressure in the range of 800 to 1200 psig, and the liquid hourly space rate in the range of 1.0 to 1.5. The copper-zinc oxide catalyst is highly sensitive to sulfur and as little as 10 ppm of sulfur as free sulfur or as simple compounds other than the ring compounds quickly deactivate the catalyst. Thus, olefin-containing streams such as catalytic cracker, thermocracker, and coker gasolines, and distillates as well as shale oil fractions can be used to produce the alcohols by hydroformylation and subsequent reduction of aldehydes to alcohols in the presence of thiophene and similar compounds usually found in these streams by maintaining the reaction conditions in the specified ranges and using the specified copper-zinc oxide catalyst described herein.

The following examples are presented to illustrate the invention without unduly restricting the same.

EXAMPLE I

A 77-hour test was made to reduce a synthetic blend of heptaldehyde in light cycle oil (boiling in the range of 420°–650° F), utilizing a reduced mixture of copper and zinc oxides containing 55.9 percent zinc and 38.7 percent (by weight) copper. The feed inlet temperature was maintained at 500° F, the pressure at 1000 psig, and the hydrogen concentration at 2000 cubic feet per barrel of charge. The heptaldehyde in the feed amounted to 30 weight percent thereof. The sulfur content in the form of thiophene amounted to 0.20 weight percent of the feed. A liquid hourly space rate of 1 was utilized. The catalyst was reduced for 8 hours at 800° F. Data obtained in the runs are presented in Table I below.

Table I

| Hours on Stream | 12 | 24 | 36 | 48 | 66 | 72 | 77 |
|---|---|---|---|---|---|---|---|
| Aldehyde conv. mol % | 99.5 | 99.4 | 99.1 | 99.2 | 99.0 | 98.7 | 99.3 |
| Alcohol yield, mol % | — | 90.2 | 94.1 | 95.0 | 90.0 | 89.6 | 93.1 |
| Efficiency | — | 90.0 | 93 | 94 | 89 | 88.5 | 92 |

The data in Table I clearly demonstrate that the catalyst is active, efficient, and is sulfur-resistant under the conditions of the run.

EXAMPLE II

A catalytic cracker heptene fraction containing 63 percent total olefins and 0.05 weight percent sulfur as thiophene was hydroformylated to yield a mixture of aldehydes and alcohols. The hydroformylation reactor product was reduced over a 38 percent CuO — 72 percent (by weight) ZnO catalyst at 500° F., one liquid hourly space rate, 1000 psig, and two standard cubic feet of hydrogen per pound of feed. The aldehyde conversion was 98-99 percent and the catalyst was still active after a throughput of 1500 volumes of feed per volume of catalyst at which time the operation was terminated.

To illustrate the fact that at reaction conditions outside of the critical ranges, desulfurization of the feed and catalyst deactivation occurs, a feed containing 480 ppm of thiophene sulfur was passed over the catalyst of Example II at a pressure of 1000 psig and a temperature of 500° F. utilizing liquid hourly space rates of 0.5, 1.0, and 1.5. The sulfur content of the effluent from these three runs was 352, 393, and 459 ppm, respectively. This clearly demonstrates that the thiophene in the feed is decomposed and deposits sulfur on the catalyst inversely to the liquid hourly space rate and that there is very little decomposition of the thiophene and sulfur deposition when utilizing the temperature, pressure, and flow rate conditions required in the invention.

EXAMPLE III

In a second test using a 5-gallon reactor, the hydroformylation product of Example II was reduced at an LHSR of 1, a temperature of 450°-500° F., and two SCF of $H_2$ per pound of feed, using different pressures. The sulfur in the effluent at various pressures of operation are presented in Table II below.

Table II

| | Sulfur, ppm |
|---|---|
| Feed | 455 |
| Product | |
| 1000 psig | 450 |
| 1500 psig | 331 |
| 1500 psig (2 passes) | 84 |

The data in Table II demonstrate the fact that thiophene is drastically decomposed with sulfur deposition on the catalyst as the pressure goes from 1000 to 1500 psig.

EXAMPLE IV

Further tests were made using a sulfur-containing aldehyde-containing feed stream, obtaining the following results utilizing 4 LHSR, 475° F., and a catalyst of the invention consisting essentially of 39 weight percent copper oxide and 61 weight percent zinc oxide:

Table III

| | Run 1 | Run 2 | Charge Feed |
|---|---|---|---|
| Pressure psig | 500 | 1000 | — |
| Product, meq/gram | | | |
| Aldehyde | 0.024 | 0.006 | 1.062 |
| Alcohol | 1.66 | 1.77 | 0.370 |
| Total | 1.684 | 1.776 | 1.432 |

These data show that by operating within my invention that highly effective conversion of aldehyde to alcohol is obtained, whereas at lower pressures the remaining unconverted aldehyde is four times higher. Total quantity as shown in the two runs is slightly higher than the total quantity shown in the charge due to the hydrolysis of acetals during hydrogenation. Hence, these runs demonstrate the necessity to restrict the lower pressure limit according to my invention as claimed.

In the aldehyde dehydrogenation process, utilizing the copper and zinc oxide catalysts and the critical operating conditions described herein, aldehydes can be dehydrogenated to the corresponding alcohol for long periods without substantial deterioration of the catalyst. The process is readily performed in other respects in accordance with the prior art dehydrogenation of aldehydes, utilizing conventional apparatus or equipment.

Certain modifications of the invention will become apparent to those skilled in the art and the illustrative details disclosed are not to be construed as imposing unnecessary limitations on the invention.

We claim:

1. A process for reducing an aldehyde to the corresponding alcohol in a hydroformylation process derived liquid feed containing at least 1 weight percent of said aldehyde and further containing at least 10 ppm and up to 1 weight percent of sulfur in the form of ring-type sulfur compounds, said aldehyde containing up to 30 carbon atoms per molecule, which comprises contacting said liquid feed under substantially liquid conditions in admixture with $H_2$ in an amount sufficient to hydrogenate said aldehyde at a temperature in the range of 450° to 550° F., a pressure in the range of 800 to 1200 psig sufficient to maintain substantially a liquid phase, and a liquid hourly space rate in the range of 1.0 to 1.5, with a catalyst comprising a mixture of the oxides or hydroxides of Zn and Cu reduced by treatment with CO, $H_2$, or mixture, wherein said catalyst initially contains 40 to 90 weight percent ZnO and 60 to 10 weight percent CuO exclusive of support, if any, prior to said reduction, and wherein said treatment with CO, $H_2$, or mixture is conducted at about 400° F. to 800° F.

2. The process according to claim 1 wherein said aldehyde is a $C_4$ to $C_{20}$ aldehyde.

3. The process according to claim 2 wherein said aldehyde is heptaldehyde, and said sulfur is in the form of thiophene.

4. The process according to claim 1 wherein said feed comprises essentially the hydroformylation reaction effluent resulting from hydroformylation of a heptene fraction containing olefins in the range of about 30 to 80 weight percent of said fraction, said effluent containing thiophene, alcohols, and aldehydes.

5. The process according to claim 4 wherein is employed a contacting temperature of 475° to 525° F., pressure of about 1000 psig, a liquid hourly space rate of 0.9 to 1.1, from 1.5 to 2.5 standard cubic feet of $H_2$ per pound of said feed.

6. The process of claim 1 wherein said mixture represents about 38 to 41 percent CuO and the balance zinc oxide prior to said reducing.

7. The process of claim 6 wherein said reducing is conducted during the process of conversion of said aldehyde to said alcohol.

* * * * *